United States Patent [19]

Stewart

[11] Patent Number: 5,695,928

[45] Date of Patent: Dec. 9, 1997

[54] RAPID IMMUNOASSAY FOR DETECTION OF ANTIBODIES OR ANTIGENS INCORPORATING SIMULTANEOUS SAMPLE EXTRACTION AND IMMUNOGENIC REACTION

[75] Inventor: Sandy J. Stewart, Durham, N.C.

[73] Assignee: Novartis Corporation

[21] Appl. No.: 343,165

[22] Filed: Nov. 22, 1994

Related U.S. Application Data

[63] Continuation-in-part of Ser. No. 165,280, Dec. 10, 1993, abandoned.

[51] Int. Cl.[6] .................................................. C12Q 1/70
[52] U.S. Cl. ........................... 435/5; 435/7.1; 435/7.2; 435/7.21; 435/7.31; 435/7.32; 435/7.4; 435/7.9; 435/7.92; 435/7.94; 435/961; 435/962; 435/968; 435/971; 435/973; 435/974; 435/975; 436/518; 436/528; 436/530; 436/532; 436/17; 436/808; 436/825
[58] Field of Search .................... 422/61, 101; 424/85, 424/8, 86, 87, 88, 89, 91, 92; 435/5, 7.1, 7.2, 7.21, 7.31, 7.32, 7.4, 7.9, 7.92, 7.94, 810, 961, 962, 968, 971, 973, 974, 975; 436/518, 528, 530, 532, 808, 809, 810, 824, 825, 826, 8, 17, 18

[56] References Cited

U.S. PATENT DOCUMENTS

| | | | |
|---|---|---|---|
| 4,108,976 | 8/1978 | Reese | 436/518 X |
| 4,366,241 | 12/1982 | Tom et al. | 435/7.92 |
| 4,376,110 | 3/1983 | David et al. | 436/513 |
| 4,803,154 | 2/1989 | Uo et al. | 435/7 |
| 4,810,648 | 3/1989 | Stalker | 435/191 |
| 4,962,023 | 10/1990 | Todd et al. | 435/7 |
| 5,006,461 | 4/1991 | Woiszwillo | 435/7.92 |
| 5,006,464 | 4/1991 | Chu et al. | 435/7.1 |
| 5,011,771 | 4/1991 | Bellet et al. | 435/7.94 |
| 5,073,341 | 12/1991 | Hargreaves | 422/58 |
| 5,122,452 | 6/1992 | Yamazaki et al. | 435/7.92 |
| 5,156,949 | 10/1992 | Luciw et al. | 435/5 |
| 5,169,757 | 12/1992 | Yamazaki et al. | 435/7.92 |
| 5,169,789 | 12/1992 | Bernstein | 436/501 |
| 5,171,537 | 12/1992 | Wainwright et al. | 422/100 |
| 5,200,321 | 4/1993 | Kidwell | 435/7.9 |
| 5,219,761 | 6/1993 | Lankow et al. | 436/177 |
| 5,283,179 | 2/1994 | Wood | 435/8 |

FOREIGN PATENT DOCUMENTS

| | | |
|---|---|---|
| 0132170 | 6/1984 | European Pat. Off. . |
| 0147848 | 12/1984 | European Pat. Off. . |
| 0268465 | 11/1987 | European Pat. Off. . |
| 0280557 | 2/1988 | European Pat. Off. . |
| 0353895 | 7/1989 | European Pat. Off. . |
| WO 89/09939 | 10/1989 | WIPO . |
| WO 94/20831 | 9/1994 | WIPO . |

OTHER PUBLICATIONS

Kodama, S., et al., "Rapid One–Step Sandwich Enzyme Immunoassay for Tissue Inhibitor of Metalloproteinases", *J. Immunol. Methods,* 127:103–108 (1990).

Mitsui Toatsu Chemicals, Inc., Abstract, "Preparation of Stable Immobilized Solid–Phase Reagents", *Chemical Abstract,* 99(19):154814z (Nov. 7, 1983).

(List continued on next page.)

*Primary Examiner*—Carol A. Spiegel
*Attorney, Agent, or Firm*—Gary M. Pace

[57] ABSTRACT

The present invention is drawn to an immunoassay capable of the rapid detection of a variety of test substances that may be present in a test sample. One feature of the invention is that extraction or isolation of the test substance occurs simultaneously with the formation of the primary antigen-test substance complex. The primary antigen-test substance complex is then captured in a solid phase format having a plurality of interstitial spaces which facilitate rapid and efficient detection. The immunoassay of the present invention works over a wide range of environmental conditions and is simple enough to be used in the absence of laboratory facilities.

71 Claims, 1 Drawing Sheet

OTHER PUBLICATIONS

Penney, C.L., et al., "Polycarbonate Membranes: A Novel Surface for Solid–phase Determinations with Utility in Field Format Serological Assays", *J. Immunol. Methods*, 123:185–192 (1989).

Salonen, E.M., et al., Abstract, "Rapid Solid–phase Enzyme Immunoassay for Antibodies to Viruses and Other Microbes: Effects of Polyethylene Glycol:," *Chemical Abstract*, 94(19):154621 (May 11, 1981).

Bergmann, A., Abstract, "Stabilizers for Endogenous Physiologically Active Peptides", *Chemical Abstract*, 118(25):248537 (Jun. 21, 1993).

RAPID IMMUNOASSAY FOR DETECTION OF ANTIBODIES OR ANTIGENS INCORPORATING SIMULTANEOUS SAMPLE EXTRACTION AND IMMUNOGENIC REACTION

The present invention is a continuation-in-part application of U.S. application Ser. No. 08/165,280 filed Dec. 10, 1993, now abandoned, the disclosures of which are herein incorporated by reference.

FIELD OF THE INVENTION

The present invention relates to rapid immunoassays for the detection of a variety of test substances.

BACKGROUND OF THE INVENTION

Immunoassays, where one or more antibodies are used to detect a test substance in a test sample, are widely known. The evolution of immunoassay methods has led to increasing sensitivity and ease of use. Despite this evolution, there remains a desire to achieve the detection and measurement of antigenic substances more rapidly and at less cost in terms of time and resources, without sacrificing sensitivity or reliability of results.

In pursuit of this desire, several forms of immunoassay have been developed. Some immunoassays have been developed which rely upon multiple antibodies, one of which may be bound to a solid material. This binding has been accomplished using nitrocellulose, polystyrene beads, plastic cloth, polycarbonate filters and the like. For example, U.S. Pat. No. 4,803,154 describes a "sandwich"-type immunoassay method in which a hydrophobic sheet is treated to create defined and delimited hydrophilic regions which can be used to bind antibodies through reactive aldehyde groups. The test sample containing the test substance is placed in contact with the treated regions having the bound antibody, which captures the test substance through an immunological reaction. Next, another antibody, to which is conjugated a means of detection, is added to the treated region and binds to the test substance immobilized on the sheet in the first step: Executing the means of detection allows one to measure the presence of the test substance in the test sample. This method is described as a "rapid" method, but requires from 60 minutes to 48 hours to complete, not including pre-assay sample preparation.

Convenient formats such as "dipsticks" have also been developed. In one example, a "dipstick" format having a polycarbonate detection membrane fused to a polyvinyl chloride sheet is used to provide an immunoassay method usable under field conditions. C. L. Penny et al. Journal of Immunological Methods 123: 185–192 (1989). In this method, the test substance is bound to a detection membrane by immersing the dipstick into the test sample, which must be a fluid. In a second step, the dipstick is immersed into a solution containing an antibody, to which is conjugated a means of detection, which is then immobilized by immunological reaction with the bound antigenic substance. In the final step, the means of detection is executed, which entails immersing the dipstick into a solution containing the appropriate detection reagents. The assay is described as requiring more than one hour to complete, not including pre-assay sample preparation.

In another example of the "sandwich"-type immunoassay, a first antibody is bound to the surface of a multiwell plate. S. Kodama et al. Journal of Immulogical Methods 127: 103–108 (1990). A previously prepared test sample is then mixed with an appropriate buffer containing a second antibody, to which is conjugated a means of detection, and the combined solution is placed in a well of the plate. In the final step, the means of detection is executed, which is accomplished by adding the appropriate detection reagent to the well. The presence of the antibody-test substance sandwich is then determined. The assay as described requires 50 minutes for completion. Sample preparation time is not included.

Other immunoassays are also known which purport to be rapid and economic, e.g., U.S. Pat. No. 4,962,023, U.S. Pat. No. 5,169,757, but all have the limitation of requiring at least one hour to complete the assay, without including the time to prepare the test sample.

Immunoassays that require less time are also known, such as the commonly available latex agglutination tests for pregnancy based on detection of human chorionic gonadotropin (hCG). One example of such a test is the B-Clone® hCG Assay manufactured by Monoclonal Antibodies and distributed by Baxter Scientific Products (McGaw, Ill.). Such tests are simple and require from a few minutes or less up to 30 minutes for detection of hCG. These tests are designed to use urine as the test sample, which does not require any preparation prior to detection of the test substance. In cases where the test sample containing the test substance is more complex, such as whole blood, feces, and plant or animal tissues, test sample preparation can be a separate and time consuming step, which can increase the time and labor needed to obtain reliable and accurate results. In these circumstances, an immunoassay that can be completed in a similar period of time, and that combines the steps of extraction with those of detection of the test substance would provide an advantage in both time and labor.

Some immunoassays have also been developed that require only a single incubation step. Such immunoassays are known as "simultaneous" immunoassays. One example of such an assay is described in U.S. Pat. No. 4,376,110. In such an assay, an antibody bound to a solid phase support is incubated with the test sample simultaneously with another antibody having a means of detection conjugated to it. Another type of immunoassay described in U.S. Pat. No. 4,376,110 is a "reverse" immunoassay, which involves the stepwise addition to the liquid test sample of first the antibody having a means of detection conjugated to it followed by the addition of an antibody bound to a solid phase support. Such immunoassays provide for ease of handling but suffer due to the potential presence of interfering substances in an unprepared test sample. Furthermore, a liquid test sample is required as the antibody-antigen reaction occurs in the liquid phase in such a immunoassay. Such "simultaneous" or "reverse" immunoassays also require an additional separation and wash steps to remove the captured antibody-test substance complex from the liquid test sample. Further examples of "simultaneous" and "reverse" immunoassays can be found in U.S. Pat. No. 5,011,771, where the need to prepare a test sample prior to immunoassay is ignored and the need to separate the captured antibody-test substance complex from the liquid test sample requires an additional sedimentation and centrifugation step. Hence, the necessity of additional steps which can require laboratory equipment can limit the usefulness of such methods for conducting immunoassays under non-laboratory conditions.

Another immunoassay has been described in U.S. Pat. No. 5,169,789 for bacteria and viruses which can be conducted in a short period of time and includes simultaneous lysing of the test sample and antibody reaction. This immunoassay uses a nitrocellulose membrane having a submicrometer pore size where the flow of the liquid containing the test substance from the sampling means to the capture membrane is limited to diffusion facilitated by an optional underlying absorbent layer. Such an immunoassay cannot be physically arranged to allow simultaneous visual determination of detection results for multiple test substances in a single assay because of the limited flow rates and opaque nature of the membrane material. Other immunoassays based on nitrocellulose with submicrometer-sized pores, such as those disclosed in U.S. Pat. No. 4,366,241 and U.S. Pat. No. 5,006,464, have similar shortcomings.

The present invention provides an immunoassay which is sensitive, reliable and economic and requires as little as 60 seconds to complete, including time to prepare the test sample and execute the means of detection of the test substance or substances.

SUMMARY OF THE INVENTION

Figure 1:
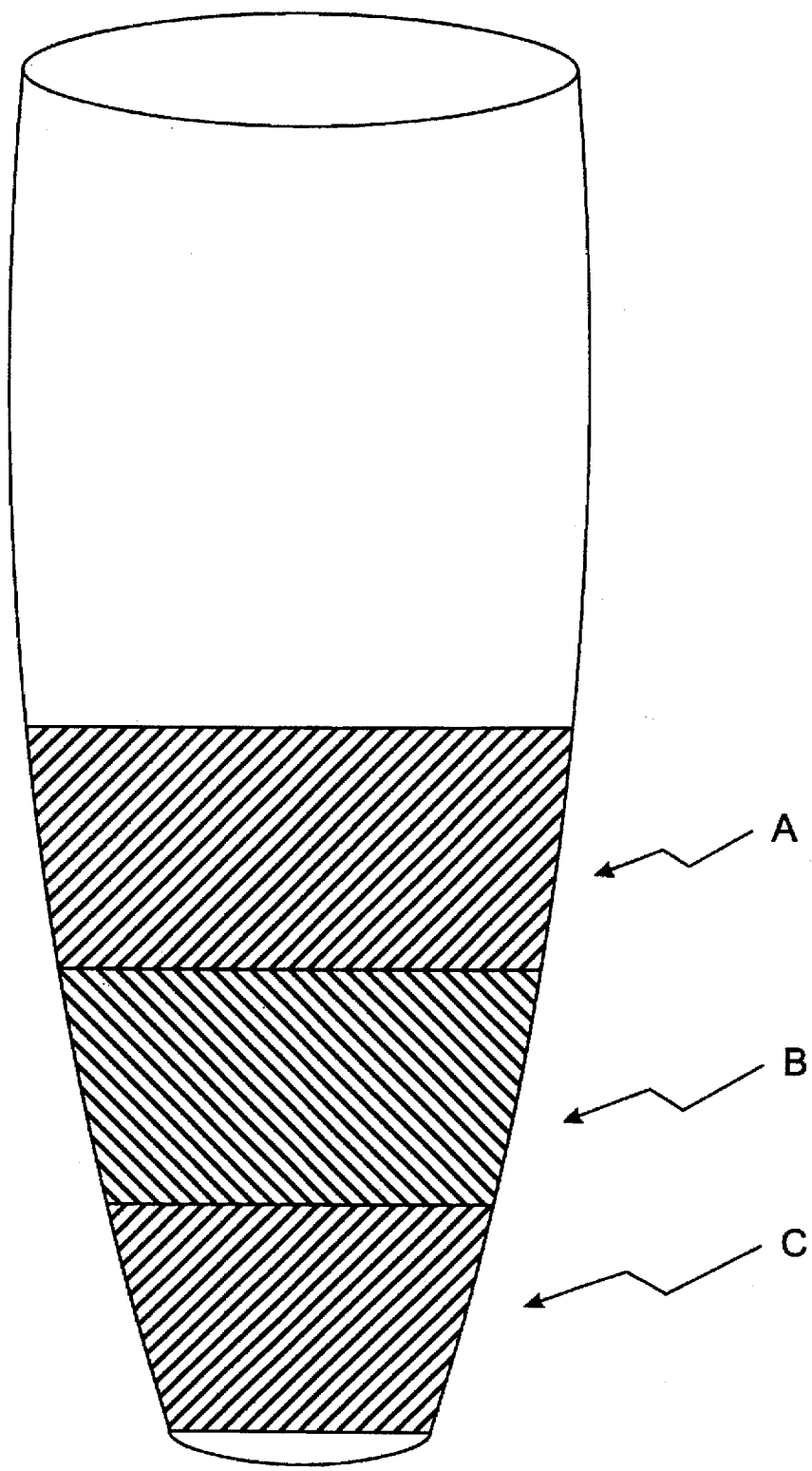
FIG. 1 shows a diagram of one embodiment of the present invention where individually prepared solid phase formats are placed in a multi-layered arrangement for the capture and detection of a primary antibody-test substance complex while simultaneously performing both a positive and negative control test. The solid phase formats are embedded inside a conventional plastic pipet tip such that they are appressed tightly against the entire inner circumference of the tip.

The present invention is drawn to an immunoassay capable of the rapid detection of a variety of test substances that may be present in a test sample. One feature of the invention is that extraction or isolation of the test substance occurs simultaneously with the formation of the primary antigen-test substance complex. The primary antigen-test substance complex is then captured in a solid phase format having a significant measurement in three dimensions to form a substantial volume with a plurality of interstitial spaces which facilitate rapid and efficient detection. Also provided is an immunoassay having solid phase formats in a multilayered arrangement that allows the simultaneous detection of multiple test substances in a single test sample. This mulitlayered arrangement may also be used for the semi-quantitative determination of the quantity of a test substance present in a test sample. The immunoassay of the present invention works over a wide range of environmental conditions and is simple enough to be used in the absence of laboratory facilities. The invention can be used for the detection of proteins, pathogens, specific antigens, specific antibodies, haptens, chemicals in the environment, or any other substance for which an antibody can be obtained. The unique method encompassed by this invention retains the sensitivity of detection of more elaborate methods without the accompanying cost in resources or time. Kits for carrying out the immunoassay are also described.

DETAILED DESCRIPTION OF THE INVENTION

The present invention relates to an immunosorbent assay that can be used to rapidly detect a test substance in a desired test sample. The test substance may be a wide variety of molecules or compounds which includes, but is not limited to, antibodies, antigens, haptens, organic chemicals, proteins, enzymes, hormones, carbohydrates, lipids, macromolecules, polymers, cells of plants, insects, mammals or any component thereof, viruses, virus subunits, toxins, pharmaceuticals, allergens, microorganisms such as bacteria, fungi, yeast, mycoplasma or any component thereof, or any test substance which is, or can be made to be, immunologically reactive.

A component is any cellular or subcellular fraction prepared or derived from any unicellular or multicellular organism. For example, a crude or purified preparation of cellular membranes would be a subcellular fraction and is, or can be made to be, immunologically reactive. Likewise, a preparation of cells can be made from isolated tissue and would be a cellular fraction which is, or can be made to be, immunologically reactive. A component may also be a subcellular fraction derived from isolated tissue, without the need of an intermediate cellular fraction step. Furthermore, a component may be a chemical or biochemical fraction of a cell or tissue, either purified or crude, which is, or can be made to be, immunologically reactive.

The immunosorbency in the assay is provided by multiple antibodies or antigens which recognize the test substance, creating a "sandwich" or complex having said test substance as a central component. An antibody is a member of the family of proteins called immunoglobins, which can specifically combine with an immunogen. Immunoglobulins are a diverse group of proteins and are found in mammals as class isotypes called IgG, IgM, IgA, IgD and IgE. Antibodies commonly have a variable region, to which an antigen binds, and a constant region which is isotype and species specific. An antigen is defined as the substance or an integral part of a substance which is immunologically recognized by the variable region of the antibody and consequently binds to it.

The first step in the immunoassay of the present invention involves extraction of the test substance from a test sample using the ExLISA buffer system, with simultaneous formation of a primary antibody-test substance complex. The primary antibody is the first ligand to be immunologically bound to said test substance. The primary antibody has a means of detection conjugated to it. Various means of detection are known in the art and will be discussed later.

The second step in the immunoassay of the present invention involves the physical capture of the primary antibody-test substance complex by an appropriate affinity ligand bound to a solid phase format. An appropriate affinity ligand depends upon the nature of the test substance and is generally capable of immunological binding to the test substance. Depending on the nature of the test substance, the appropriate affinity ligand may be either a secondary antibody (to capture a complementary antigen or another, complementary antibody) or an antigen (to capture its complementary antibody). In the present invention the solid phase format is porous and has a significant measurement in three dimensions to form a substantial volume, which possesses a plurality of interstitial spaces. The appropriate affinity ligand is bound to the solid phase format. "Solid phase format" is used to mean the physical organization or arrangement of the matrix that constitutes the capture media of the immunoassay. Optionally, a tertiary antibody may be added when the test substance to be detected in the immunoassay is an antigen. This tertiary antibody would be recognized immunologically by the secondary antibody bound to the solid phase format. The tertiary antibody would also immunologically recognize the test substance. Solid phase capture formats prepared in this way have increased sensitivity and consequently have greater levels of detection than solid phase capture formats prepared without the tertiary antibody.

The third step in the immunoassay of the present invention involves the detection of the primary antibody-test substance complex which has been captured by the appropriate affinity ligand(s) attached to the solid phase format. This is afforded by the means of detection conjugated to the primary antibody, which remains associated with the affinity ligand-test substance-primary antibody complex which is formed upon physical capture.

The rapid detection afforded by the present invention is achieved in part by performing simultaneously both, 1) extraction of the test substance from the desired test sample, and 2) binding of said test substance to the primary antibody.

In order to achieve the combined utility of allowing for both extraction of the test substance from the test sample and formation of the primary antibody-test substance complex to occur simultaneously it was necessary to create a buffer system which balances the strength required of an extraction method with the delicacy of antibody-antigen binding. The term "ExLISA" is used to refer to this unique buffer system which combines the components necessary for ex-traction of a test substance from a test sample with the components necessary to perform an immunoassay similar to that found with an ELISA. The development of the ExLISA buffer system overcomes the obstacles present with typical extraction buffers which are inhibitory to antibody-antigen binding, such as the inclusion of sulfhydryl reducing agents like dithiothreitol (DTT). Furthermore, the ExLISA buffer system overcomes the additional problem present with typical immunoassay buffers in that they do not effect a satisfactory test sample extraction. The immunoassay procedure is therefore accentuated by the ExLISA buffer system which allows the primary antibody-test substance binding reaction to occur in much less time than with conventional methods. In most cases, the complete immunoassay, including test sample extraction, can be completed in about one minute. Because extraction of the test substance from the test sample and formation of the primary antibody-test substance complex occur simultaneously, the resulting ExLISA buffer system has a faster reaction time than the typical immunoassay buffer system and is only limited by the avidity of the antibodies employed.

The ExLISA buffer system of the present invention is capable of both optimal extraction of the test substance to be detected from a test sample and optimal primary antibody-antigen binding in a single step. The ExLISA buffer system comprises a buffer to control pH, a detergent, a salt, a chelator, a stabilizing agent, a phenolic inhibitor, a protease inhibitor, and a protein which is not recognized by any of the antibodies used in the assay.

The buffer selected for the ExLISA buffer system must be suitable for both extraction of the test substance from the test sample and optimal formation of the primary antibody-test substance complex. Preferred buffers are of the inorganic type which maintain pH between about 6.5 and about 9.0, preferably about 7.5 to about 8.5. Optimal primary antibody-test substance complex formation occurs within this range, and the solubility of most test substances is also optimal within this range. Preferred buffers include sodium carbonate, sodium borate or Tris-saline. The preferred range of concentrations of the buffer are from about 10 mM to about 200 mM, more preferably about 25 to about 100 mM, and should be sufficient to provide adequate buffering capacity without being too high and inhibiting formation of the primary antibody-test substance complex. In one preferred embodiment, the buffer is 50 mM sodium carbonate at pH 8.5.

A suitable detergent is added to the ExLISA buffer system to facilitate the dissolution of cellular material during the extraction process. The concentration must be carefully chosen so that the dissolution of cellular material is balanced against the denaturing effects of the detergent, and is preferred to be in the range of about 0.01 to about 0.2% (w/v), more preferably in the range of about 0.01% to about 0.1% (w/v). In addition, a preferred detergent is of the non-ionic type so as not to inhibit the formation of the primary antibody-test substance complex. Suitable detergents may be selected from TRITON® X-100 non-ionic detergent polyoxyethylene ether, TWEEN® 20 non-ionic detergent polyopyethylene sorbitan, NP-40 nonylphenoxy polyethoxy ethanol or MEGA-8 octanoyl-N-methylglucamide. In one embodiment of the invention, the detergent is TRITON® X-100 at 0.05% (w/v).

An appropriate concentration of salt is chosen for inclusion in the ExLISA buffer system such that it provides optimal formation of the primary antibody-test substance complex. It is preferred that a physiological saline solution be used at a concentration ranging from about 25 mM to about 175 mM, more preferably from about 100 mM to about 175 mM. Preferred salts may be selected from sodium chloride, potassium chloride and the like. In one embodiment of the invention, the salt is sodium chloride at a concentration of 140 mM.

A chelator should also be used in the ExLISA buffer system in order to remove multivalent ions having a charge of positive-2 or greater from solution released by the extraction of the test substance from the test sample. Multivalent ions removed by said chelator that may be present in biological or environmental test samples are $Ca^{2+}$, $Mg^{2+}$, $Zn^{2+}$, $Al^{3+}$, etc. Removal of the multivalent ions prevents protein precipitation in the solution. It is preferred that the chelator be present in a concentration ranging from about 0.5 mM to about 10 mM, more preferably from about 1 mM to about 5 mM. An appropriate chelator may be selected from EDTA (ethylenediaminetetraacetic acid), EGTA (ethylene glycol-bis(β-amino-ethyl ether) N,N,N',N'-tetraacetic acid), etc. In one embodiment of the invention, the chelator is EDTA at 5 mM.

A stabilizing agent is added to the ExLISA buffer system to maintain the stability and activity of the primary antibody-test substance complex and the detection means which is conjugated to the primary antibody. The concentration of the stabilizing agent is critical so as not to slow down the formation of the primary antibody-test substance complex. Preferred stabilizing agents are agar, agarose, polyethylene glycol, glycerol, ethylene glycol, etc. The preferred concentration of stabilizer is from about 0.01% to about 20% (w/v), more preferably from about 1% to about 10% (w/v). In one embodiment of the invention the stabilizing agent is polyethylene glycol (3 kilodalton) at 1% (w/v).

A phenolic compound inhibitor is added to the ExLISA buffer system to remove phenolic compounds that are released into solution upon extraction of the test substance from the test sample. Phenolic compounds will precipitate proteins, interfering with dissolution of the test substance as well as with the formation of the primary antibody-test substance complex. Preferred phenolic compound inhibitors include the insoluble, high molecular weight, cross-linked form of polyvinylpyrrolidone known as polyvinylpolypyrrolidone (PVPP), sodium borate or polyethylimine. A preferred concentration of phenolic compound inhibitor is from about 0.01% to about 1% (w/v), more preferably from about 0.05% to about 0.5% (w/v). In one embodiment of the invention, PVPP is used at a concentration of 0.15% (w/v).

A protease inhibitor is added to the ExLISA buffer system in order to prevent digestion of proteins by proteases that are released by extraction of the test substance from the test sample. Such proteases could destroy the primary antibody as well as proteinaceous test substances. Protease inhibitors which inhibit either serine-, cysteine-, or aspartate-type proteases are suitable for inclusion in the ExLISA buffer system. Suitable protease inhibitors are PEFABLOC® 4-(2-Aminoethyl)-benzenesulfonyl fluoride hydrochloride, PMSF (phenylmethylsulfonyl fluoride), TLCK (N-tosyl-L-lysine chloromethyl ketone), TPCK (N-tosyl-L-phenylalanine chloromethyl ketone), α-caproic acid, leupeptin, benzamidine, antipain or pepstatin. The preferred concentration of protease inhibitor is from about 0.01 mM to about 1 mM, more preferably from about 0.1 mM to about 0.5 mM. In one embodiment of the invention, PEFABLOC® protease inhibitor (Boehringer Mannhein) at a concentration of 0.5 mM is used.

A protein which is not recognized by any of the antibodies used in the assay is also present in the ExLISA buffer system. This unrecognized protein allows the immunological blocking of non-specific antibody binding by molecules or compounds released by extraction of the test sample. This said unrecognized protein also provides further protection of proteins against protease attack by being exogenously supplied in a higher concentration than other proteins released by extraction of the test sample. Suitable unrecognized proteins are bovine serum albumin (BSA), ovalbumin, casein or fetal bovine serum. Preferred concentrations of unrecognized protein range from about 0.05% to about 5% (w/V), more preferably from about 0.1% to about 2% (w/v). In one embodiment of the invention, BSA is added at 0.5% (w/v).

It is desirable for maximum convenience, economy of antibody use and range of applications that the test sample be extracted with the ExLISA buffer in a minimal volume. Thus it is recognized that the extraction can be carried out in a small test tube, centrifuge tube, or any similarly small vessel. The extraction of the test substance from the test sample can be facilitated by the use of a glass rod, pestle, vortexing, sonication, homogenization or any other physical force which enhances destruction of the integrity of the test sample. In addition, glass beads, carborundum, silica or any other coarse material may be added to further enhance the breakdown of test sample integrity. In one example, a plastic microfuge tube and matching pestle combination, which has been widely used for tissue maceration and extraction, has been found suitable for use in the present invention.

Another unique feature of the present invention is the solid phase format used to capture the primary antibody-test substance complex formed during extraction of the test substance from the test sample using the ExLISA buffer. "Solid phase" as used in the art generally means a non-porous surface of a microtiter plate or tube wall as well as the marginally porous surface of nitrocellulose. Hence, the solid phase of an immunoassay in the art essentially describes a capture media with a two dimensional character. "Solid phase format" as used herein means the physical organization or arrangement of the matrix that constitutes the capture media of the immunoassay of the present invention. This term "solid phase format" is therefore used herein to distinguish the present invention from those uses of "solid phase" present in the art.

Since it is preferred that the test sample be extracted with a minimal quantity of ExLISA buffer, a solid phase format is required that is suitable for the efficient capture of the primary antibody-test substance complex. It is further desired that the solid phase format used must have a significant measurement in three dimensions to form a substantial volume, thus providing a large effective surface area within a plurality of interstitial spaces through which the extract of the test sample can be drawn. In addition, the solid phase format used as the capture media for the primary antibody-test substance complex should be sufficiently porous so that liquids flow actively and quickly through the entire volume. This requires that the solid phase format have a pore size in the micrometer range or greater, as opposed to the submicron range. This highly porous, three-dimensional "format" allows exceptionally effective capture of the primary antibody-test substance complex in the rapid immunoassay of the present invention. A further advantage of the porosity and physical arrangement of the solid phase format is that, particularly in the tip arrangement (see FIG. 1 ), there is no need for the use of a filtration or centrifugation step to effect removal of particulates, etc., which may be formed in the extraction of tissue that can clog the submicrometer-sized pores of conventional solid phases.

Many materials are available which can be fashioned accordingly and used as appropriate solid phase formats for the present invention. Some of these materials are cellulose acetate, polyester coated with polystyrene, cellulose, nitrocellulose and nylon. In one preferred embodiment, the ACT-10® cylindrical filter composed of cellulose fibers and available from Hydros, Inc., Falmouth, Mass., is used as the solid phase format. The ACT-10® is a cylindrical shape with a diameter of approximately 4 mm and a height of approximately 6 mm, with a pore size of approximately 20–30 micrometers. Several examples are given below in which the ACT-10® is used as the solid phase format.

In another preferred embodiment, the cylindrical filter composed of polyester coated with polystyrene and available from American Filtrona, Richmond, is used as the solid phase format. This filter is also cylindrical in shape with a diameter of approximately 4 mm and a height of approximately 6 mm, with a pore size of approximately 20–30 micrometers. This solid phase format can be superior to cellulose acetate for certain immunoassays since the polystyrene coating provides an increase in the quantity of functional groups used for covalent binding. The polyester coated with polystyrene also possesses a much increased physical integrity. In a further advantage over solid phase formats composed of cellulose acetate, the use of polyester allows for antibody to be covalently bound, dried with a cryoprotectant, and then stored dry until use. Cellulose acetate, which expands and contracts due to moisture availability, must remain in liquid at all times once covalently bound with antibody. When using the polyester coated with polystyrene, the prepared solid phase format can be stored under dry conditions for 15 months. The polyester coated with polystyrene solid phase format has been employed in all of the arrangements and assays mentioned herein, producing equal or better assay results than those obtained with cellulose acetate.

The selected solid phase format must be prepared for use in the immunoassay of the present invention by binding the appropriate affinity ligand to it. It is the binding of the affinity ligand to the solid phase format which provides the capacity to capture the primary antibody-test substance complex. In one embodiment of the invention, the appropriate affinity ligand is bound to the solid phase format by first creating amino binding groups through alkylation on the solid phase format. Suitable alkylating agents are aldehydes and N-maleimides. Once the solid phase format is prepared a secondary antibody is then covalently attached to the solid phase format through the chemically reactive amino group. In the case of aldehydes, a reversible Schiff base is first formed between the aldehyde and an amino group on the secondary antibody. This bond is then stabilized through reductive alkylation with a low concentration of sodium cyanoborohydride. The thus prepared solid phase format may then be used for the capture of primary antibody-test substance complexes.

Alternatively, prior to capture of the primary antibody-test substance complex a tertiary antibody may be immunologically bound to the secondary antibody. The tertiary antibody is chosen such that it immunologically recognizes the test substance, immunologically binding to it and thereby capturing the primary antibody-test substance complex.

In another embodiment of the invention, the solid phase format is first prepared as described above to create reactive aldehyde groups. Once prepared, strepavidin is covalently attached to the reactive groups and reduced with a low concentration of sodium cyanoborohydride. The thus prepared solid phase format may then be used for the capture of biotin labeled secondary or tertiary antibody which is bound to the primary antibody-test substance complex.

In a further embodiment of the invention, the solid phase format is first prepared as described above. Once prepared, an appropriate antigen is covalently bound to the solid phase format through a means suitable to the chemical nature of the chosen antigen. The solid phase format can then be used for the capture of antibodies in the extract which recognize the bound antigen.

It is not a requirement of the present invention that the affinity ligand(s) be bound to the solid phase format in a covalent manner. Antibodies, other proteins and many antigens can be adsorbed to solid phase formats through electrostatic or other molecular forces. Solid phase formats prepared in this way can be equally effective in capturing a test substance present in the test sample. It is possible, however, that long term stability of the bond between the affinity ligand(s) and the solid phase format may be jeopardized because such bonds are weaker than covalent bonds.

The thus prepared solid phase format-affinity ligand complex is used to capture the primary antibody-test substance complex obtained through extraction of the test sample with the ExLISA buffer system. The present invention provides a unique capture method when compared to existing methods. Capture of the primary antibody-test substance complex proceeds by drawing an appropriate volume of the extract through the interstitial spaces of the solid phase format which has bound to it the appropriate affinity ligand(s) used in the immunoassay of the present invention. Drawing an appropriate volume of the extract through the large effective surface area afforded by the porous solid phase format provides exceptionally effective capture of the primary antibody-test substance complex.

In one embodiment of the present invention, the solid phase format is embedded inside a plastic pipet tip such that the solid phase format is appressed tightly against the entire inner circumference of the tip, as depicted in FIG. 1. This creates, in essence, a low volume "chromatographic" column. As the extract prepared from the test sample using the ExLISA buffer is drawn into the pipet tip using a standard pipettor, the extract is drawn through the entire volume of the solid phase format. This arrangement presents an extremely large surface area to which is bound the appropriate affinitiy ligand(s), allowing for a quick and dynamic capture of the primary antibody-test substance complex which formed during extraction of the test substance from the test sample using the ExLISA buffer system. This permits the use of relatively small volumes of prepared extract of less than 20 µl while simultaneously providing a binding capacity of approximately 10 µg or more of test substance. This unique combination of low volume and high binding capacity allows for a high concentration recovery of the primary antibody-test substance complex.

The solid phase format may also be employed in both eye dropper barrels and syringe barrels with equal results. Additionally, both the eye dropper and syringe arrangements allow for aspiration and expulsion by their connected bulb or plunger without the need for additional mechanical devices. Both arrangements also allow for the use of larger solid phase formats for capture of the primary antibody-test substance complex, which permits the covalent binding of increased concentrations of antibody with the consequent capture of increased amounts of test substance.

Another arrangement that may be employed is a 96-well microplate template which has wells with open-end bottoms in the form of tiny funnels, such as that available from Polyfiltronics, Inc., Rockland, Mass., and marketed under the name FILTAPLATE®. This multiwell plate may be seated into a small vacuum unit which allows a vacuum to be drawn from the top of the microplate through the funnels and into a reservoir under the microplate. The above described polyester coated with polystyrene solid phase formats, which are particularly suited to this arrangement because of their sturdy physical integrity, are placed in each well of the multiwell plate so that the solid phase format is appressed tightly against the circumference of the inner wall of the well. Up to 96 test samples may be handled as a single assay. This arrangement allows for both qualitative and quantitative measurements of a test substance, depending upon the choice of whether a soluble or insoluble reaction product is produced by the means of detection used (see discussion below). The qualitative version of such a rapid immunoassay according to the present invention employs a secondary or tertiary antibody covalently bound to the solid phase format, which is then placed in a well of the multiwell plate. The test sample is then extracted in ExLISA buffer containing the appropriate primary antibody-enzyme conjugate and added to the well. Vacuum is then drawn through the well containing the polyester filter element. The well is then washed by vacuum and a substrate which produces an insoluble reaction product is added and allowed to react with the enzyme bound to the captured test substance complex before removal by vacuum. The resulting colorimetric detection allows for a qualitative, visual determination of the presence of the test substance.

The quantitative version of a rapid immunoassay based on this arrangement is identical to the qualitative version described above, with two exceptions. First the vacuum device which the microplate is seated into is modified to accept the addition of a second 96-well microplate directly under and in line with the first, so that each well of the first microplate is directly above the corresponding well of the second microplate. The second plate can be any conventional 96-well plate as used for ELISA-type assays. After capture of the test substance complex by the solid phase format in the well and subsequent washing, the second plate is then placed into the modified vacuum device. An enzyme substrate which produces a soluble reaction product is then added to the well and allowed to react with the test substance complex before drawing the solution containing the reaction product into the second microplate. The second microplate is then removed and placed in any microplate reader for quantitative analysis of the resulting solution. By performing a typical standard curve comparison in other wells containing similarly prepared solid phase formats, very specific and sensitive quantitative analysis can be performed quickly and reliably. This arrangement is also amenable to the use of both fluorescent markers conjugated to streptavidin which are then coupled to primary antibody labelled with biotin and also chemiluminescent substrates for alkaline phosphatase conjugated to primary antibody. The resulting sensitivities are at least 1000-fold greater than those possible using the cellulose actetate solid phase format in the pipet tip arrangement.

Once one solid phase format is prepared by binding of the appropriate affinity ligand(s), it may also be combined with other similarly prepared solid phase formats in a multi-layer arrangement. This multilayered arrangement permits the detection of several different primary antibody-test substance complexes in a single extract. This arrangement also permits the inclusion of positive or negative control layers allowing the determination of positive and negative control results within a single assay step. When used to detect more than one test substance in a single assay, the ExLISA buffer system would be modified to include a variety of conjugated primary antibodies which are specific for the range of test substances to be detected in the test sample.

Multiple solid phase formats can be used to provide a semi-quantitative immunoassay by binding increasing levels of secondary and/or tertiary antibodies to each of several solid phase formats which, for example, would correspond to low, medium and high levels of test substance. Depending on the level of test substance present in the test sample, one (low), two (medium) or three (high) prepared solid phase formats will exhibit a positive reaction according to the means of detection used.

Detection of the captured primary antibody-test substance complex, and hence determination of the presence or absence of the test substance in the test sample, may be accomplished through a wide variety of methods that are well known to the art. Useful references describing the general and specific principles of detection in immunoassays may be found in E. Harlow and D. Lane, *Antibodies, A Laboratory Manual*, Cold Spring Harbor Laboratory, New York, 1988, or in E. T. Maggio, Ed., *Enzyme-Immunoassay*, CRC Press, Florida, 1980. Both citations are herein incorporated by reference.

Detection techniques can be divided into direct and indirect methods. In the direct method, the primary antibody is labeled by conjugating to it a means of detection; the primary antibody conjugate is then use to bind directly to the test substance. Examples of such detection means useful in the direct method are radioactive iodine, a variety of enzymes using chromogenic substrates, biotin, fluorochromes, metals such as colloidal gold, or the biosynthesis of the primary antibody in the presence of radioactive amino acid precursors. In the indirect method, the primary antibody is not conjugated to any means of detection. Instead, its binding to the test substance is detected by a secondary reagent, for example using labeled anti-immunoglobin antibodies or labeled protein A.

The choice of the means of detection depends upon the assay conditions, ease of use, availability of reagents, stability of reagents and the required sensitivity of the assay. Preferred in the present invention is the use of direct methods as a means of detection. As a broad generalization relative to available direct methods as a means of detection, enzyme labels offer the advantage of an instant visual result and great sensitivity making them useful for quantitative assays but are more difficult to use in a quantitative assay because of the need to measure accurately the rate of reaction. Radio-iodine labeling of primary antibodies can give strikingly accurate quantitative results in immunoassay procedures but stringent safety procedures are required for its use. Fluorochromes require a means of ultraviolet light excitation and detection by flourimetry or fluorescence microscopy, although they can provide high resolution in applications such as immunocytochemistry. Metal labels such as gold colloids has become more widely available in many useful forms. Gold is biologically inert and has a good charge density, allowing it to bind readily to the charged groups on the primary antibody.

In one preferred embodiment of the present invention, enzymes are conjugated to the primary antibody as a means of detection. Antibodies can be readily labeled by covalent coupling to enzymes. See e.g., S. Avrameas, *Enzyme Markers: Their linkage with proteins and use in immunohistochemistry*, Histochem. J. 4: 321–330, 1972. Since enzyme reactions intrinsically amplify the detection signal, such conjugates can be exceptionally sensitive. Detection levels may be as low as the picomolar range.

A large number of enzymes have been used to label antibodies. The most commonly used are horseradish peroxidase, alkaline phosphatase and β-galactosidase. Urease and glucose oxidase are also in limited use. The ideal enzyme for use as a means of detection should be inexpensive, very stable and easily conjugated. The ideal enzyme should also have a high catalytic activity and react with a range of substrates that yield both soluble products and insoluble products. In a preferred embodiment of the present invention, bovine intestinal alkaline phosphatase is used as the means of detection. It should be recognized, however, that many suitable methods of detection exist, and it is encompassed within the scope of the invention that any of several methods of detection can be used.

Conjugation of means of detection are well known in the art. Enzymes may be conjugated to primary antibodies by any one of several common methods. In the glutaraldehyde method, glutaraldehyde couples to the enzyme and to the primary antibody through reactive amino groups available on each protein. See e.g., S. Avrameas, *Coupling of enzymes to proteins with glutaraldehyde*, Immunochemistry 6: 43–52, 1969. In the periodate method, periodate treatment of carbohydrates opens the ring structure and allows these moieties to bind free amino groups present on the protein. See e.g., P. K. Nakane and A. Kawaoi, *Peroxidase labeled antibody: A new method of conjugation*, J. Histochem. Cytochem. 22: 1084–1091, 1974. Conjugation of amino groups on the enzyme may also be covalently attached to thiol groups introduced on the antibody through reaction with SPDP (N-succinimidyl-3-[2-pyridyldithio]propionate), reduction and formation of a pyridyl disulfide bridge. A. J. Cumber, et al. *Preparation of antibody-toxin conjugates*, Methods Enzymol. 112:207 (1985). The preferred method of conjugation of alkaline phosphatase in the present invention is the glutaxaldehyde method.

Alternatively, the means of detection conjugated to the primary antibody can be one of several fluorochromes. Four fluorochromes are in common use, fluorescein, rhodamine, Texas red and phycoerytherin. The fluorochromes are conjugated to the primary antibody by reaction with ammonium chloride in DMSO (dimethyl sulfoxide). See e.g., J. W. Goding, Conjugation of antibodies with fluorochromes, J. Immunol. Methods 13: 215–226, 1976. In one preferred embodiment of the present invention, the isocyanate derivatives of either fluorescein (FITC) or rhodamine (TRITC) are used.

The substrate for enzymatic means of detection may produce either a soluble or insoluble reaction product. An insoluble enzyme reaction product has the advantage of remaining within the solid phase format after reaction. This permits visual observation of the immunoassay results. The use of an insoluble reaction product also has the benefit of permitting layering of differently prepared formats in the present embodiment (see FIG. 1 ). The insolubility of the reaction product prevents leaching of the product from one layer to the next, allowing simultaneous assay for multiple primary antibody-test substance complexes or for semi-quantitative analysis. Alternatively, if the substrate used produces a soluble enzyme reaction product, then the product may be leached from the solid phase format which captured the primary antibody-test substance complex and its presence detected by, for example, spectrophotometry, so that the amount of the primary antibody-test substance complex present may be quantitatively determined.

The immunoassay of the present invention may be used to detect a wide variety of test substances present in, or originating from, plants, mammals, insects, microorganisms, soil, air, water or the environment in general. The test substance may be a wide variety of molecules or compounds which includes, but is not limited to, antibodies, antigens, haptens, organic chemicals including herbicides, proteins, enzymes, hormones, carbohydrates, lipids, macromolecules, polymers, cells of plants, insects, mammals or any part thereof, viruses, virus subunits, toxins, pharmaceuticals, allergens, microorganisms such as bacteria, fungi, yeast, mycoplasma or any part thereof, or any test substance which is, or can be made to be, immunogenically active.

The general immunoassay procedure using the present invention begins with obtaining a test sample to be assayed for the presence or absence of the test substance. The test sample is placed in a suitable vessel in the presence of the combined primary antibody and ExLISA buffer system having an appropriate amount and composition. The test sample may be obtained by any means suitable to the nature of the test sample. For example, plant tissue may be obtained by cutting, slicing, tearing, punch out or clipping. Blood samples, on the other hand, could be obtained by a simple liquid transfer step. Mammalian tissue samples may be obtained by any of the wide variety of biopsy procedures available.

It is a requirement of the present invention that the primary antibody be combined with the ExLISA buffer system prior to its use. If many test samples are prepared at one time for comparison it is desirable that the amount of the test sample be reasonably consistent from sample to sample. This is important in that both the volume of the ExLISA buffer system used and the amount of antibody must be maintained in a suitable ratio to each other in order to obtain the maximum level of sensitivity and extraction of the test substance. Furthermore, to obtain the most precise comparisons from test sample to test sample, roughly equivalent amounts of sample should be obtained for each assay.

Once the test sample is combined with the ExLISA buffer system plus primary antibody it may be necessary to provide some physical force to disrupt the integrity of the test sample and facilitate extraction of the test substance. Some examples of means to facilitate the extraction of the test substance from the test sample are by the use of a glass rod, pestle, vortexing, sonication, or homogenization. In addition, glass beads, carborundum, silica or any other coarse material may optionally be added to further enhance the breakdown of test sample integrity. One advantage of the present invention is that the ExLISA buffer system permits optimal reaction of the primary antibody with the test substance immediately upon its release from the test sample during the extraction process. When the test sample, ExLISA buffer system and primary antibody are chosen within the guidelines of the present invention the test substance in the extract can be prepared for capture within about 5 to about 60 seconds, more preferably within about 5 to about 30 seconds, most preferably within about 10 to about 15 seconds.

Capture of the primary antibody-test substance complex formed in the step above occurs by drawing the extract through the interstitial spaces of the solid phase format that has been previously prepared according to the methods described above. Drawing an appropriate volume of the extract through the large effective surface area afforded by the porous solid phase format provides exceptionally effective capture of the primary antibody-test substance complex. The extract is held within the interstitial spaces of the solid phase format for about 5 to about 60 seconds, more preferably for about 5 to about 30 seconds, most preferably for about 10 to about 15 seconds. The extract is expelled from the solid phase format after the appropriate amount of time.

The solid phase format which has captured the primary antibody-test substance complex is then washed once with an appropriate washing buffer. This has the effect of removing residual chemicals and non-captured substances from the solid phase format. The washing of the solid phase format is achieved by either drawing the washing buffer into it and then expelling or by forcing the washing buffer through it.

After washing the solid phase format containing the captured primary antibody-test substance complex, any reagent which is required for the means of detection is added. The immunoassay of the present invention may use any of the wide variety of means of detection described above and known in the art. In a preferred embodiment of the invention, an enzyme is conjugated to the primary antibody as the means of detection, then the appropriate substrate should be drawn into the solid phase format. The substrate then reacts with the conjugated enzyme, producing a detectable product. Detection by this means is achieved generally within about 5 minutes or less.

In one preferred embodiment, the present invention is useful for determining the presence or absence of a test substance in plant tissue according to the following steps:

1. A sharp-capped microfuge tube is used to obtain a small sample of plant tissue by closing the cap over the plant part to be sampled, causing a portion of the plant part to be excised from the body of the plant and being contained in the tube.
2. Add 250 µl of the ExLISA buffer system, which was previously combined with the appropriate primary antibody and which is conjugated to alkaline phosphatase, to the sampling tube. Macerate the tissue for approximately 5 to 10 seconds.
3. Draw the extract into an ACT-10® solid phase format (Hydros, Inc., Falmouth, Mass.) which has been prepared with the appropriate affinity ligand(s) as described above. Hold this mixture for approximately 5 to 15 seconds to facilitate capture of the primary antibody-test substance complex and then expel.
4. Wash the tip with 1 ml of a washing buffer (10 mM Tris-TRIZMA pH 8.0, 0.05% w/v TWEEN® 20 nonionic detergent, 0.02% w/v sodium azide) by forcing the buffer down through the tip.
5. Draw into the tip approximately 50 µl of the enzyme substrate, nitroblue tetrazolium plus bromochloroindole phosphate.
6. Wait 5 to 10 minutes to allow for full color development and record results.

Alternatively, if it is desired to detect antibodies in a test sample, then the appropriate antigen would be covalently bound to the solid phase format and using the same principles of single step extraction and antigen reaction coupled with effective capture of the antigen and detection thereof.

For example, isotyping of immunoglobulins, such as IgG or IgM, in order to determine the antibody population within a given serum can be accomplished rapidly with the present invention. Antibodies prepared to each immunoglobulin class can be bound to the appropriate solid phase format. Individual solid phase formats could be prepared for each immunoglobulin class and then each one is place within the piper tip in a multilayered arrangement (see FIG. 1). Upon simultaneous extraction of the serum and formation of the primary antibody-immunoglobulin complex using an appropriate ExLISA buffer, the test sample is drawn through each individual layer in order to capture a different primary antibody-immunoglobulin complex within the interstitial spaces of each individual layer of prepared solid phase format. A standard detection method such as any of those listed above is then used to indicate the presence of different immunoglobulins in the test sample.

Another example of the use of the present invention to detect antibodies in serum is the detection of antibodies to human immunodeficiency virus (HIV). Either formalin-fixed HIV or coat protein is bound to an appropriate format. Serum is extracted and formation of the primary antibody-test substance complex is accomplished using an appropriate ExLISA buffer system containing, e.g., an anti-human antibody as the primary antibody. The extract is drawn through the porous solid phase format to which is bound the non-viable virus or coat protein, capturing the primary antibody-HIV-specific antibody complex. Detection then occurs by any of several previously described means.

The present invention, combining the elements of simultaneous extraction and primary antibody-test substance complex formation, capture of said complex, and detection of said complex provides an immunoassay which can be performed in no more than a few minutes and under a wide range of environmental conditions. It is simple enough to be used in the absence of laboratory conditions—in the field, office, greenhouse, farm, or home. The invention can be used for the detection of expressed proteins, pathogens, specific antigens, specific antibodies, chemicals in the environment, or any other substance for which an antibody, either monoclonal or polyclonal can be obtained. The unique method encompassed by this invention retains the sensitivity of detection of more elaborate methods without the accompanying cost in resources or time. The immunoassay of the present invention can be performed by any person according to simple instructions, allowing for use at home, office, field or any other location.

In order to maximize the utility of the present invention, it is desirable to have the immunoassay assembled in a kit form. Such a kit is convenient to use as it contains all the reagents necessary to obtain results. In one embodiment of the present invention, a kit for immunoassay is comprised of a microfuge tube for each test sample, a pipet tip for each test sample having embedded in it a solid phase format prepared with an appropriate affinity ligand(s) for the capture of the primary antibody-test substance complex in a multilayered arrangement along with a solid phase format prepared as a positive control and a solid phase format prepared as a negative control, a pestle suitable for grinding a test sample in the microfuge tube, a dispensing bottle of ExLISA buffer system which optionally may or may not have the primary antibody conjugated to a means of detection pre-diluted in it, a dispensing bottle of washing buffer, a 1 ml disposable transfer pipet for each test sample to be used for the washing buffer, and a dispensing bottle of an appropriate reagent to be used with the means of detection conjugated to the primary antibody. Kits containing sufficient parts for up to 20 test samples are convenient for use under field conditions.

In another embodiment of the invention, a kit for large scale use may be prepared such that the components are prepared in bulk and placed in quantities of 20 or more. Larger volumes of reagents are supplied, or are supplied in 2-fold to 10-fold concentrations, and additional disposable pipets and pestles are added to the kits.

The following examples further describe the materials and methods used in carrying out the invention and the subsequent results. They are offered by way of illustration, and their recitation should not be considered as a limitation of the claimed invention.

EXAMPLES

A. ExLISA Buffer

One preferred example of the ExLISA buffer system is composed of 50 mM NaCO$_3$ at pH 8.5, 140 mM NaCl, 5 mM EDTA, 0.05% TRITON® X-100 non-ionic detergent, 0.15% PVPP (w/v), 1. % PEG (3 kilodalton), 0.5 mMPE-FABLOC® protease inhibitor, 0.5% BSA. This example has been found to be widely useful for the extraction of plant tissue or cells, effectively combining extraction and formation of the primary antibody-test substance complex into one simultaneous process. The reagents are commonly available through the indicated chemical supply houses.

| 50 mM | NaCO3 pH 8.5 | (Sigma Chem.) |
| 140 mM | NaCl | (Sigma Chem.) |
| 5 mM | EDTA | (Sigma Chem.) |
| 0.05% | TRITON ® X-100 | (Sigma Chem.) |
| 0.15% | PVPP | (Sigma Chem.) |
| 1.0% | PEO (3 kd) | (Sigma Chem.) |
| 0.5% | BSA | (Sigma Chem.) |
| 0.5 mM | PEFABLOC ® | (Boehringer Mannheim) |

Prior to use, the ExLISA buffer in this example is combined with a primary antibody, which has conjugated to it alkaline phosphatase as one example of a detection means. The primary antibody is chosen such that it immunologically recognizes the test substance and may be prepared from any source, for example, goat, rabbit, rat or mouse. Immunoaffinity purification may be used to obtain purified primary antibody, and calf intestine alkaline phosphatase may be conjugated to it using a modified glutaraldehyde method of Avrameas, supra. The conjugated primary antibody is tilered to determine the working dilution for use in the assay according to the present invention. The appropriate dilution must be determined for each batch of primary antibody made, but is generally in the range of from 1:100 to 1:1000, made in ExLISA buffer. This primary antibody conjugate in ExLISA buffer instantaneously binds to the test substance when the plant tissue or cells are macerated in its presence.

B. Detection of *Bacillus thurigiensis* kurstaki (Btk) endotoxin expressed in leaf tissue The solid phase format, one example of which may be purchased from Hydros, Inc. (Falmouth, Mass.) and is known commercially as ACT-10®, which is capable of binding primary amine groups present on proteins, as described above. The secondary antibody covalently bound to the solid phase format was immunopurified goat anti-rabbit antibody (commercially available from a multitude of vendors) at a 100 μg/ml concentration in a borate-saline (100 mM boric acid, 25 mM sodium borate, 75 mM sodium chloride, pH 8.5) buffer at 4 C. overnight. Unbound goat anti-rabbit antibody was then removed from the solid phase format and bound goat anti-rabbit antibody was covalently attached to the format by reduction of the Schiffs base with 20 mM sodium cyanoborohydride for 2 to 4 hours. Any remaining active sites on the solid phase format were then blocked with blocking buffer ( 3% w/v bovine serum albumin, 0.02% w/v sodium azide, 10 mM sodium phosphate, 140 mM sodium chloride, pH 7.5) for at least 1 hour at 4 C. The blocking buffer was then removed and immunoaffinity purified rabbit anti-Btk tertiary antibody was added at 15 μg/ml in diluent buffer (1% w/v bovine serum albumin, 0.02% sodium azide, 0.05% TWEEN® 20 non-ionic detergent, 10 mM sodium phosphate, 140 mM sodium chloride, pH 7.5) and incubated at 4 C. overnight. The tertiary antibody binds to the secondary antibody in a normal antibody-antigen reaction.

Three layers of solid phase format were embedded in a pipet tip (as shown in FIG. 1) for the Btk endotoxin protein assay. The bottom solid phase format layer was an assay positive control which consisted of calf intestine alkaline phosphatase covalently attached to the solid phase format. The solid phase format layer above the positive control layer is the negative control which consists of adsorbed bovine serum albumin. The top solid phase format layer is the layer used to capture the primary antibody-test substance complex from the extract, which is described above. The three layers of solid phase format embedded in the pipet tip were stored in tip storage buffer (25 mM Tris, 140 mM NaCl, pH 7.8, 2% w/v BSA, 0.05% w/v TWEEN® 20 non-ionic detergent, 0.02% w/v $NaN_3$) until the test sample extract was prepared (can be stored up to 6 months). The storage buffer was removed by aspiration from the prepared solid phase format immediately prior to its use.

The leaf tissue of the test plant was obtained by snapping the lid of a 1.5 ml microfuge tube on a leaf, which removes a small circular area of tissue. This test sample was kept cool when the assay could not be performed within one hour, or if the ambient temperature was above 90° F. This tissue was then macerated in the presence of 250 μl of the ExLISA buffer described in Example A, above, using a Kontes® (Vineland, N.J.) plastic pestle for maceration by a firm rotating action for approximately 5 seconds. During extraction, the primary goat anti-Btk antibody binds to the Btk endotoxin protein released from the tissue by maceration with the pestle in the microfuge tube. The extract was then drawn through the interstitial spaces of the prepared solid phase format, allowing the primary antibody-Btk complex to be captured by the secondary antibody-tertiary antibody complex bound to the solid phase format. The extract was held in the solid phase format for at least 15 seconds and then expelled to a waste vessel. The extract may remain in the solid phase format for up to one hour at room temperature before expelling, although beyond 2–3 minutes the sensitivity only increases marginally. After capture the solid phase format was washed with 1 ml of wash buffer (10 mM Tris-TRIZMA pH 8.0, 0.05% w/v TWEEN® 20 non-ionic detergent, 0.02% w/v sodium azide). The solid phase format was then saturated with nitroblue tetrazolium plus bromochloroindole phosphate, which is a single component substrate for alkaline phosphatase available from the chemical supply house Kirkegaard & Perry. Depending upon the amount of Btk endotoxin protein present, the reaction may begin almost immediately. However, generally the reaction was allowed to proceed for at least 5 minutes before results were recorded. Only the full sandwich complex will be identified by the substrate, which is specific for alkaline phosphatase. Care must be taken to keep the tip with the enzyme substrate in it away from UV light as the substrate is light sensitive.

The result for a particular test sample was determined by recording the color present in each of the three layers. The bottom solid phase format layer, as the positive control, should always turn dark blue color when the assay is performed. The solid phase format layer above the positive control is the negative control and should always remain white to slightly gray in color when assayed. The top solid phase format layer is for capturing, and subsequently detecting, the presence of the primary antibody-Btk protein complex and will turn color only in its presence. Therefore, a dark-blue unknown solid phase format represented a positive plant for BT presence and no color change (white, or slightly gray as dictated by the negative control) represented a BT negative plant. If the positive control (bottom solid phase format layer) does not turn dark blue or the negative control (middle solid phase format layer) does not remain white or light gray, then the assay MUST be repeated as this indicates a false reading.

Over 500 plants have been tested for the presence of the Btk endotoxin by both the rapid immunoassay of the present invention under field conditions and by conventional laboratory-based ELISA. A perfect correlation was observed between the two assays, showing that the rapid immunoassay is as sensitive and reliable as the more time-consuming and resource-intensive ELISA.

C. Detection of cucumber chitinase in leaf tissue

This immunoassay follows the same procedure as described above with the exception of the antibodies used. To assay for the presence of the expressed cucumber chitinase protein in leaf tissue, goat anti-mouse secondary antibody was covalently bound to the desired solid phase format by Shiffs base base formation with aldehyde groups, reduction by cyanoborohydride and blocking of unreacted sites with bovine serum albumin. A mixture of three immunopurified monoclonal mouse tertiary antibodies against cucumber chitinase were bound to the goat anti-mouse secondary antibody by way of a normal antibody-antigen reaction. This prepared solid phase format was then used to capture the primary antibody-test substance complex. The prepared solid phase format was embedded into a pipet tip, along with a solid phase format layer for the positive control and a separate solid phase format layer for the negative control, as described above. The ExLISA buffer system was the same as described in Example A, above, except that immunoaffinity purified rabbit anti-cucumber chitinase primary antibody was added to it. This primary antibody was conjugated to alkaline phosphatase as described above. The extract prepared by macerating the tissue in the presence of the ExLISA buffer system was then drawn into the interstitial spaces of the prepared solid phase format. Upon treatment with the enzyme substrate, the upper solid phase format layer turned dark blue when the primary antibody-chitinase protein complex was present.

Using the principles described in Example D, below, the expression of chitinase has also been detected in a semi-quantitative manner using a multi-layered arrangements of solid phase formats prepared with increasing levels of secondary antibody. Pr-1 basic protein, with is often endogenously expressed in plants concomitantly with chitinase in response to pathogen infection, was determined simultaneously with chitinase as described above when solid phase formats prepared with the appropriate secondary antibody were combined in a tip arrangement.

D. Detection of fungal pathogens of wheat

This immunoassay follows the same procedure as previously described with the exception the antibodies used for detection of the pathogen. Immunoaffinity purified goat anti-sheep secondary antibody was bound to the appropriate solid phase format through reactive aldehyde groups, the Schiffs base was reduced by sodium cyanoborohydride, and unreacted sites were blocked by the addition of bovine serum albumin. Purified sheep tertiary antibody against *Septoria tritici* was bound to the goat anti-sheep secondary antibody by way of a normal antibody-antigen reaction. The ExLISA buffer system was the same as described in Example A, above, except that immunoaffinity purified sheep anti-*Septoria tritici* conjugated to alkaline phosphatase was added to it. The extract prepared by macerating the tissue in the presence of the ExLISA buffer system was then drawn into the interstitial spaces of the prepared solid phase format. Upon treatment with the enzyme substrate, the upper solid phase format layer mined dark blue when the primary antibody-*Septoria tritici* antigen complex was present.

Semi-quantitative detection of the level of *Septoria tritici* or *Septoria nodorum* infestation of wheat plants was also achieved using the present immunoassay by adjusting the levels of the secondary and/or tertiary antibodies covalently bonnd to the solid phase format. Each of three solid phase formats were prepared with decreasing levels of secondary antibody specific for either *Septoria tritici* or *Septoria nodorum*, depending on the species of pathogen detected. The quantity of secondary antibody which corresponds to low, medium, or high infestation levels was pre-determined by a sandwich ELISA using the same antibodies in order to calibrate the rapid immunoassay. The three prepared solid phase formats, along with solid phase formats prepared as positive and negative controls, were placed in a conventional plastic pipet tip in a stacked and contiguous manner similar to that shown in FIG. 1. A leaf extract was prepared in the ExLISA buffer system containing a primary antibody-enzyme conjugate where the primary antibody was specific for either *Septoria tritici* or *Septoria nodorum*, again depending on the species of pathogen detected. The extract containing the test substance was drawn through the five stacked and contiguous solid phase formats as prepared above. The extract was expelled, the tip was washed, and enzyme substrate was drawn into the tip to allow for visual assessment. Differing levels of Septoria resulted in either one, two or three prepared solid phase formats becoming colorimetrically positive. In other words, a low level of Septoria infestation resulted in one prepared solid phase format being positive, a medium level of infestation resulted in two formats being positive and a high level resulted in three formats being positive.

Both *Septoria tritici* and *Septoria nodorum* were also be detected simultaneously in the same assay from the same test sample. By using two prepared solid phase formats, one covalently bound with a secondary antibody to detect one pathogen and the other covalently bound with secondary antibody to detect the other pathogen, it was possible to distinguish if one or both pathogens were present. Both prepared solid phase formats were placed in a single pipet tip, along with solid phase formats prepared as positive and negative controls, similar to that depicted in FIG. 1. The leaf sample was homogenized in the presence of ExLISA buffer and two primary antibody-enzyme conjugates, each recognizing one of the two Septoria species. The test sample extract was drawn through the tip, expelled, the tip was washed, and then enzyme substrate was drawn into the tip for colorimetric visualization. When both species of Septoria were present in the test sample, both the solid phase formats prepared with secondary antibody reacted positively. When only one special of Septoria was present in the test sample, then only the solid phase format prepared with the secondary antibody recognizing that species reacted positively.

Detection and semi-quantitation of *Pseudocercosporella herpotrichoides* (Eyespot disease in wheat) can also be accomplished using the rapid immunoassay. The immunoassay uses polyclonal antibodies specific for *P. herpotrichoides* as the primary antibody with an enzyme conjugated to it as a means of detection and as the secondary antibody covalently bound to solid phase formats. Wheat tissue is homogenized in ExLISA buffer containing the antibody-enzyme conjugate and is drawn through the prepared solid phase formats as outlined above. Levels of Eyespot disease infestation can be semi-quantitated within a single assay as described above for Septoria, or the presence of *P. herpotrichoides*, *S. tritici*, and *S. nodorum* can all be detected within a single rapid immunoassay.

E. Detection of fungal pathogen (Sigatoka) of banana

This immunoassay will be exactly the same as described in Example D, except with appropriate antibodies. Both monoclonals and polyelonals are used for the primary, secondary and tertiary antibodies, with solid phase format preparation, capture of the primary antibody-test substance complex and detection with alkaline phosphatase as the means of detection.

F. Detection of insect gut receptors

The purpose of this immunoassay is to determine the absence or presence of specific toxin binding receptors found in the gut membrane of a single individual of the insect Plutella. Each toxin has a specific binding receptor in the gut membrane. This immunoassay follows a similar procedure as that described above with the exception that a purified specific endotoxin isolated from *Bacillus thuringiensis* is bound to a appropriate solid phase format through interaction with an aldehyde group, the Schiffs base is reduced by sodium cyanoborohydride, and the unreacted sites are blocked by the addition of bovine serum albumin. The ExLISA buffer system is prepared with immunoaffinity purified rabbit primary antibody which immunologically recognizes Plutella brush border membrane vesicles. The primary antibody is conjugated to alkaline phosphatase. A single insect is placed in a microfuge tube and macerated with a pestle in the ExLISA buffer system containing the primary antibody. The resulting extract is drawn into the interstitial spaces of the prepared solid phase format by aspiration and is captured by the *Bacillus thuringiensis* endotoxin which is covalently bound to the solid phase format. Different *Bacillus thuringiensis* endotoxins are covalently bound to separate solid phase formats, and each separate solid phase format is embedded in layers in the piper tip. Although the rabbit anti-brush border membrane primary antibody will non-specifically bind all insect gut receptors present in the extract, only those which bind the specific endotoxin present in a specific format layer will be captured by that layer. Therefore, only a primary antibody-gut receptor complex specific for the endotoxin bound in a particular format layer will be captured by that layer, and produce a positive result with detection by alkaline phosphatase as exhibited by the development of a dark blue color in that layer. The variation in gut receptor binding for different *Bacillus thuringiensis* endotoxins may be quickly determined by observing which solid phase format layers give a positive reaction and which give a negative reaction.

G. Detection of Antibodies to Brucella abortus in Bovine Serum

Brucella abortus is a major bacterial pathogen of cattle and causes bovine brucellosis, a veterinary disease with significant economic consequences. The disease is highly contagious and subject to government quarantine. A rapid means of determining the presence of the disease would be by detecting the presence of antibodies against the Brucella pathogen in bovine serum and would be advantageous in monitoring and controlling the spread of the disease. This has the benefit of detecting antibody over pathogen where the titer of the pathogen is not stable. Partially purified lipopolysaccharide from Brucella abortus or a crude extract of Brucella abortus is prepared and adsorbed onto an appropriate solid phase format. Lipopolysaccharide binding to the solid phase format may possibly be enhanced by the use of leetins. Any remaining binding sites on the solid phase format must be blocked with a protein other than bovine serum albumin, such as ovalbumin or casein. The thus prepared solid phase format is embedded in a multi-layered arrangement into a pipet tip along with a separate solid phase format for a negative control (middle layer, to which ovalbumin has been bound) and for a positive control (bottom layer, to which alkaline phosphatase has been bound). An appropriate amount of bovine senan is diluted into ExLISA buffer to which has been added goat antibovine immunoglobulin primary antibody conjugated to alkaline phosphatase. The extract of the test sample thus prepared is then drawn into the interstitial spaces of the multilayered solid phase formats. After the extract is held for about 15 seconds it is expelled. The pipet tip is then washed with washing buffer. The solid phase format is then saturated with nitroblue tetrazolium plus bromochloroindole phosphate, which is a substrate for alkaline phosphatase. Depending upon the amount of antibody to Brucella abortus present in the serum sample, the reaction may begin within one minute. However, generally the reaction proceeds for at least 10 minutes before results are recorded.

H. Detection of Herbicides in Soil and Water Samples

This immunoassay follows the same procedures as described above with the exception of the antibodies used. To assay for the presence of the herbicides such as metalochlor or sulfonylurea in soil or water, the monoclonal antibodies described in U.S. Ser. No. 08/359,689, a continuation of U.S. Ser. No. 08/035,872, filed Mar., 23, 1993, which immunologically recognize metalochlor, and in U.S. Ser. No. 07/988,509, filed Dec. 10, 1992, which immunologically recognize member of the class of herbicides known as sulfonylureas, are used as primary and secondary antibodies. Secondary antibody is covalently bound to the desired solid phase format by Shiffs base formation with aldehyde groups, reduction by cyanoborohydride and blocking of unreacted sites with bovine serum albumin. This prepared solid phase format is then used to capture the primary antibody-herbicide complex. The prepared solid phase format is embedded into a pipet tip, along with a solid phase format layer for the positive control and a separate solid phase format layer for the negative control, as described above. The ExLISA buffer system was the same as described in Example A, above, except that immunoaffinity purified primary antibody which immunologically recognizes the herbicide to be detected is added to it. This primary antibody was conjugated to alkaline phosphatase as described above. In the case of soil samples, the herbicide must first be extracted using procedures known in the art, whereupon the extract so made is combined with ExLISA buffer. Water samples may be used without preparation, or may be concentrated by known methods prior to combining with ExLISA buffer. The resulting combined mixture is then drawn into the interstitial spaces of the prepared solid phase format. Upon treatment with the enzyme substrate, the upper solid phase format layer will turn dark blue when the primary antibody-herbicide complex is present.

Using the principles described in Example D, above, the presence of herbicides may also be detected in a semi-quantitative manner using a multi-layered arrangement of solid phase formats prepared with increasing levels of secondary antibody. In addition, the presence of more than one herbicide in the test sample may be determined simultaneously as described above when solid phase formats prepared with the appropriate secondary antibody are combined in a tip arrangement.

The extraction process using the ExLISA buffer system has proven to be as successful as various other extraction methods currently in use. This was shown by direct comparisons of standard methods and the method encompassed by the present invention. Immunoassays for Bacillus thuringiensis kurstaki endotoxin, Bacillus thuringiensis tenebrionis endotoxin, PR1a protein, cucumber chitinase and phosphinothricin acetyltransferase produced similar quantitative values when extracts were prepared using the ExLISA buffer system as compared to those obtained from the use of standard extraction techniques. Hence, the extraction method using the ExLISA buffer system produces identical results when compared with standard methods.

All publications and patent applications mentioned in this specification are indicative of the level of skill of those skilled in the art to which this invention pertains. All publications and patent applications are herein incorporated by reference to the same extent as if each individual publication or patent application was specifically and individually indicated to be incorporated by reference.

Although the foregoing invention has been described in some detail by way of illustration and example for purposes of clarity of understanding, it will be obvious that certain changes and modifications may be practiced within the scope of the appended claims.

What is claimed is:

1. An ExLISA buffer system which is capable of supporting simultaneous sample extraction and antigen-antibody reaction consisting essentially of:
   (a) a buffer;
   (b) a non-ionic detergent present at a concentration of about 0.01 to about 0.2% (w/v);
   (c) a salt in an amount effective to provide a physiological saline solution and present at a concentration of about 25 mM to about 175 mM;
   (d) a chelator in an amount effective to remove multivalent ions;
   (e) a stabilizing agent in an amount effective to maintain stability and activity of an antibody in said antigen-antibody reaction and present at a concentration from about 0.01 to about 20% (w/v);
   (f) a phenolic compound inhibitor;
   (g) a protease inhibitor; and,
   (h) a protein in an amount effective to immunologically block non-specific antibody binding and present at a concentration from about 0.05 to 5% (w/v).

2. The ExLISA buffer system of claim 1 wherein said buffer is selected from sodium carbonate, sodium borate or Tris-saline.

3. The ExLISA buffer system of claim 1 wherein said detergent is selected from polyoxyethylene ether, polyoxyethylene sorbitan, nonylphenoxy polyethoxy ethanol or octanoyl-N-methylglucamide.

4. The ExLISA buffer system of claim 1 wherein said salt is selected from sodium chloride or potassium chloride.

5. The ExLISA buffer system of claim 1 wherein said chelator is selected from ethylenediaminetetraacetic acid or ethylene glycol-bis(β-amino-ethyl ether) N,N,N',N'-tetraacetic acid.

6. The ExLISA buffer system of claim 1 wherein said stabilizing agent is selected from agar, agarose, polyethylene glycol, glycerol or ethylene glycol.

7. The ExLISA buffer system of claim 1 wherein said phenolic inhibitor is selected from polyvinylpolypyrrolidone, sodium borate or polyethylimine.

8. The ExLISA buffer system of claim 1 wherein said protease inhibitor is selected from 4-(2-Aminoethyl)-benzenesulfonyl fluoride hydrochloride, phenylmethylsulfonyl fluoride, N-tosyl-L-lysine chloromethyl ketone, N-tosyl-L-phenylalanine chloromethyl ketone, α-caproic acid, leupeptin, benzamidine, antipain or pepstatin.

9. The ExLISA buffer system of claim 1 wherein said protein is selected from bovine serum albumin, ovalbumin, casein or fetal bovine serum.

10. The ExLISA buffer system of claim 1 further comprising a primary antibody capable of binding to said test substance wherein said primary antibody is conjugated to a means of detection.

11. The ExLISA buffer system of claim 10 wherein said means of detection is an enzyme.

12. The ExLISA buffer system of claim 11 wherein said enzyme is selected from alkaline phosphatase, peroxidase, or β-galactosidase.

13. The ExLISA buffer system of claim 10 wherein said means of detection is a fluorochrome.

14. The ExLISA buffer system of claim 13 wherein said fluorochrome is selected from fluorescein isothiocyanate, tetramethylrhodamine isothiocyanate, Texas red, phycoerythrin.

15. An immunoassay for detection of at least one test substance in a plant sample comprising the steps of:
 (a) extracting the plant sample with the ExLISA buffer of claim 1 in the presence of a primary antibody which immunologically recognizes said test substance in said extract to form a primary antibody-test substance complex, wherein said primary antibody is conjugated to a means of detection;
 (b) providing a cylindrical solid phase format having a diameter of about 4 millimeters, a height of about 6 millimeters and a pore size of about 20–30 millimeters with a plurality of interstitial spaces and further having immobilized therein a secondary antibody capable of
  (i) immunologically recognizing said test substance or
  (ii) a tertiary antibody which immunologically recognizes said test substance;
 (c) contacting the extract of step (a) with
  (i) the cylindrical solid phase format of step (b)(i) or
  (ii) the cylindrical solid phase format of step (b)(ii) and said tertiary antibody to capture said primary antibody-test substance complex;
 (d) washing the cylindrical solid phase format of step (c) with a buffer; and
 (e) detecting said test substance by detecting the presence of said captured primary antibody-test substance complex.

16. The immunoassay of claim 15 wherein said test substance is selected from a bacterium, an insect, a fungus, a virus, a plant cell, a protein, a carbohydrate, a hormone, a pharmaceutical, a lipid, a herbicide, or an immunoreactive component thereof.

17. The immunoassay of claim 16 wherein said bacterium is *Brucella abortus*.

18. The immunoassay of claim 16 wherein said insect is Plutella.

19. The immunoassay of claim 16 wherein said fungus is selected from the group consisting of *Septoria tritici*, *Septoria nodorum*, *Pseudocercosporella herpotrichoides* and a fungal pathogen causing Sigatoka of banana.

20. The immunoassay of claim 16 wherein said virus is human immunodeficiency virus.

21. The immunoassay of claim 16 wherein said protein is selected from immunoglobin, cucumber chitinase, or *Bacillus thuringiensis* endotoxin.

22. The immunoassay of claim 15 wherein said solid phase format is selected from cellulose acetate, polyester coated with polystyrene, cellulose, or nylon.

23. The immunoassay of claim 22 further comprising a plurality of said cylindrical solid phase formats wherein said cylindrical solid phase formats are arranged in stacked and contiguous layers wherein each layer captures a different primary antibody-test substance complex.

24. The immunoassay of claim 22 further comprising a plurality of said cylindrical solid phase formats wherein said cylindrical solid phase formats are arranged in stacked and contiguous layers wherein each layer captures a different quantity of said primary antibody-test substance complex.

25. The immunoassay of claim 15 wherein said means of detection is an enzyme.

26. The immunoassay of claim 25 wherein said enzyme is selected from alkaline phosphatase, peroxidase, or β-galactosidase.

27. The immunoassay of claim 25 wherein said enzyme is reacted with a substrate therefore to produce a detectable insoluble reaction product.

28. The immunoassay of claim 25 wherein said enzyme is reacted with a substrate therefore to produce a detectable soluble reaction product.

29. The immunoassay of claim 1 wherein said means of detection is a fluorochrome.

30. The imunoassay of claim 29 wherein said fluorochrome is selected from fluorescein isothiocyanate, tetramethyl, Texas red, or phycoerythrin.

31. An immunoassay for detection of at least one test substance in a test sample comprising the steps of:
 (a) extracting the test sample with the ExLISA buffer of claim 1 in the presence of a primary antibody which immunologically recognizes said test substance in said extract to form a primary antibody-test substance complex, wherein said primary antibody is conjugated to a means of detection;
 (b) providing a cylindrical solid phase format having a diameter of about 4 millimeters, a height of about 6 millimeters and a pore size of about 20–30 millimeters with a plurality of interstitial spaces and further having immobilized therein a secondary antibody capable of
  (i) immunologically recognizing said test substance or
  (ii) a tertiary antibody which immunologically recognizes said test substance;
 (c) contacting the extract of step (a) with
  (i) the cylindrical solid phase format of step (b)(i) or
  (ii) the cylindrical solid phase format of step (b)(ii) and said tertiary antibody to capture said primary antibody-test substance complex;
 (d) washing the cylindrical solid phase format of step (c) with a buffer; and (f) detecting said test substance by detecting the presence of said captured primary antibody-test substance complex.

32. The immunoassay of claim 31 wherein said test substance is selected from a bacterium, an insect, a fungus, a virus, a plant cell, a protein, a carbohydrate, a hormone, a pharmaceutical, a lipid, a herbicide, or an immunoreactive component thereof.

33. The immunoassay of claim 32 wherein said insect is Plutella.

34. The immunoassay of claim 32 wherein said fungus is selected from the group consisting of *Septoria tritici*, *Septoria nodorum*, *Pseudocercosporella herpotrichoides* and a fungal pathogen causing Sigatoka of banana.

35. The immunoassay of claim 32 wherein said protein is selected from immunoglobin, cucumber chitinase, or *Bacillus thuringiensis* endotoxin.

36. The immunoassay of claim 31 wherein said solid phase format is selected from cellulose acetate, polyester coated with polystyrene, cellulose, or nylon.

37. The immunoassay of claim 36 further comprising a plurality of cylindrical solid phase formats and wherein said cylindrical solid phase formats are arranged in stacked and contiguous layers wherein each layer captures a different primary antibody-test substance complex.

38. The immunoassay of claim 36 further comprising a plurality of cylindrical solid phase formats and wherein said cylindrical solid phase formats are arranged in stacked and contiguous layers wherein each layer captures a different quantity of said primary antibody-test substance complex.

39. The immunoassay of claim 31 wherein said means of detection is an enzyme.

40. The immunoassay of claim 39 wherein said enzyme is selected from alkaline phosphate, peroxidase, or β-galactosidase.

41. The immunoassay of claim 39 wherein said enzyme is reacted with a substrate therefore to produce a detectable insoluble reaction product.

42. The immunoassay of claim 39 wherein said enzyme is reacted with a substrate therefore to produce a detectable soluble reaction product.

43. The immunoassay of claim 31 wherein said means of detection is a fluorochrome.

44. The immunoassay of claim 43 wherein said fluorochrome is selected from fluorescein isothiocyanate, tetramethylrhodamine isothiocyanate, Texas red, or phycoerythrin.

45. An immunoassay for detection of at least one test substance in a test sample comprising the steps of:
(a) extracting the test sample with the ExLISA buffer of claim 1 in the presence of a primary antibody which immunologically recognizes said test substance in said extract to form a primary antibody-test substance complex, wherein said primary antibody is conjugated to a means of detection;
(b) providing a cylindrical solid phase format having a diameter of about 4 millimeters, a height of about 6 millimeters and a pore size of about 20–30 millimeters with a plurality of interstitial spaces, and further having immobilized therein an antigen capable of immunologically recognizing said test substance;
(c) contacting the extract of step (a) with cylindrical solid phase format of step (b);
(d) washing the cylindrical solid phase format of step (c) with a buffer; and
(f) detecting said test substance by detecting the presence of said captured primary antibody-test substance complex.

46. The immunoassay of claim 45 wherein said test substance is an antibody.

47. The immunoassay of claim 45 wherein said solid phase format is selected from cellulose acetate, polyester coated with polystyrene, cellulose, or nylon.

48. The immunoassay of claim 47 further comprising a plurality of cylindrical solid phase formats and wherein said cylindrical solid phase formats are arranged in stacked and contiguous layers wherein each layer captures a different primary antibody-test substance complex.

49. The immunoassay of claim 47 further comprising a plurality of cylindrical solid phase formats and wherein said cylindrical solid phase formats are arranged in stacked and contiguous layers wherein each layer captures a different quantity of said primary antibody-test substance complex.

50. The immunoassay of claim 45 wherein said means of detection is an enzyme.

51. The immunoassay of claim 50 wherein said enzyme is selected from alkaline phosphatase, peroxidase, or β-galactosidase.

52. The immunoassay of claim 50 wherein said enzyme is reacted with a substrate therefore to produce a detectable insoluble reaction product.

53. The immunoassay of claim 50 wherein said enzyme is reacted with a substrate therefore to produce a detectable soluble reaction product.

54. The immunoassay of claim 45 wherein said means of detection is a fluorochrome.

55. The immunoassay of claim 54 wherein said fluorochrome is selected from fluorescein isothiocyanate, tetramethylrhodamine isothiocyanate, Texas red, or phycoerythrin.

56. A kit for detection by immunoassay of at least one test substance in a test sample comprising in packaged combination:
(a) a means of extraction of said test substance in the presence of a primary antibody which immunologically recognizes said test substance wherein said primary antibody is conjugated to a means of detection;
(b) a cylindrical solid phase format having a diameter of about 4 millimeters, a height of about 6 millimeters and a pore size of about 20–30 micrometers with a plurality of interstitial spaces capable of capturing a complex formed by said primary antibody and said test substance;
(c) a vessel containing the ExLISA buffer system of claim 1;
(d) reagents reactive with said means of detection to produce a detectable reaction product;
(e) a means of dispensing said reagents.

57. The kit of claim 56 wherein said test substance bound by said primary antibody is selected from a bacterium, an insect, a fungus, a virus, a plant cell, a protein, a carbohydrate, a hormone, a pharmaceutical, a lipid, a herbicide, or an immunoreactive component thereof.

58. The kit of claim 57 wherein said bacterium is *Brucella abortus*.

59. The kit of claim 57 wherein said insect is Plutella.

60. The kit of claim 57 wherein said fungus is selected from the group consisting of *Septoria tritici*, *Septoria nodorum*, *Pseudocercosporella herpotrichoides* and a fungal pathogen causing Sigatoka of banana.

61. The kit of claim 57 wherein said virus is human immunodeficiency virus.

62. The kit of claim 57 wherein said protein is selected from immunoglobulins, cucumber chitinase, or *Bacillus thuringiensis* endotoxin.

63. The kit of claim 56 wherein said solid phase format is selected from cellulose acetate, polyester coated with polystyrene, cellulose, or nylon.

64. The kit of claim 63 further comprising a plurality of cylindrical solid phase formats and wherein said cylindrical solid phase formats are arranged in stacked and contiguous layers wherein each layer captures a different primary antibody-test substance complex.

65. The kit of claim 63 further comprising a plurality of cylindrical solid phase formats and wherein said cylindrical solid phase formats are arranged in stacked and contiguous layers wherein each layer captures a different quantity of said primary antibody-test substance complex.

66. The kit of claim 56 wherein said means of detection is an enzyme.

67. The kit of claim 66 wherein said enzyme is selected from alkaline phosphatase, peroxidase, or β-galactosidase.

68. The kit of claim 66 wherein said enzyme is reacted with a substrate therefore to produce a detectable insoluble reaction product.

69. The kit of claim 66 wherein said enzyme is reacted with a substrate therefore to produce a detectable soluble reaction product.

70. The kit of claim 56 wherein said means of detection is a fluorochrome.

71. The kit of claim 70 wherein said fluorochrome is selected from fluorescein isothiocyanate, tetramethylrhodamine isothiocyanate, Texas red, or phycoerythrin.

* * * * *

UNITED STATES PATENT AND TRADEMARK OFFICE
CERTIFICATE OF CORRECTION

PATENT NO  :  5,695,928
DATED      :  December 9, 1997
INVENTOR(S):  Sandy J. Stewart, Durham, NC It is certified that error appears in the above-identified patent and that said Letters Patent is hereby corrected as shown below:

In claim 15 at column 23, line 49, change "20-30 millimeters" to -- 20-30 micrometers --.

In claim 31 at column 24, line 55, change "20-30 millimeters" to -- 20-30 micrometers --.

In claim 45 at column 25, line 57, change "20-30 millimeters" to -- 20-30 micrometers --.

Signed and Sealed this

Twelfth Day of January, 1999

Attest:

*Attesting Officer*          Acting Commissioner of Patents and Trademarks